United States Patent [19]

Sheen et al.

[11] Patent Number: 5,606,113
[45] Date of Patent: Feb. 25, 1997

[54] ACOUSTIC METHODS TO MONITOR SLIVER LINEAR DENSITY AND YARN STRENGTH

[75] Inventors: Shuh-Haw Sheen; Hual-Te Chien, both of Naperville; Apostolos C. Raptis, Downers Grove, all of Ill.

[73] Assignee: The University of Chicago, Chicago, Ill.

[21] Appl. No.: 301,346

[22] Filed: Sep. 6, 1994

[51] Int. Cl.⁶ .............................. G01N 9/24; G01N 29/00
[52] U.S. Cl. .............................. 73/32 A; 73/597; 73/159; 19/240
[58] Field of Search ..................... 73/32 A, 597, 73/579, 599, 78, 73, 159, 160, 290 V; 19/22, 240

[56] References Cited

U.S. PATENT DOCUMENTS

| | | | |
|---|---|---|---|
| 3,984,895 | 10/1976 | Grice, Jr. .............................. | 73/32 A |
| 4,481,820 | 11/1984 | Thomann .............................. | 73/597 |
| 4,672,851 | 6/1987 | Blessing et al. ......................... | 73/597 |
| 4,766,647 | 8/1988 | Ackermann, Jr. ....................... | 73/703 |
| 5,062,299 | 11/1991 | Davis et al. ............................ | 73/597 |
| 5,125,514 | 6/1992 | Oehler et al. ........................... | 73/627 |
| 5,136,202 | 8/1992 | Carenzo et al. ....................... | 310/323 |
| 5,164,710 | 11/1992 | Anderegg et al. ..................... | 310/323 |
| 5,181,421 | 1/1993 | Kline ..................................... | 73/597 |

*Primary Examiner*—Hezron E. Williams
*Assistant Examiner*—Helen C. Kwok
*Attorney, Agent, or Firm*—Mason, Kolehmainen, Rathburn & Wyss

[57] ABSTRACT

Methods and apparatus are provided for monitoring sliver and yarn characteristics. Transverse waves are generated relative to the sliver or yarn. At least one acoustic sensor is in contact with the sliver or yarn for detecting waves coupled to the sliver or yarn and for generating a signal. The generated signal is processed to identify the predefined characteristics including sliver or yarn linear density. The transverse waves can be generated with a high-powered acoustic transmitter spaced relative to the sliver or yarn with large amplitude pulses having a central frequency in a range between 20 KHz and 40 KHz applied to the transmitter. The transverse waves can be generated by mechanically agitating the sliver or yarn with a tapping member.

15 Claims, 4 Drawing Sheets

5,606,113

ACOUSTIC METHODS TO MONITOR SLIVER LINEAR DENSITY AND YARN STRENGTH

CONTRACTUAL ORIGIN OF THE INVENTION

The United States Government has rights in this invention pursuant to Contract No. W-31-109-ENG-38 between the United States Government and Argonne National Laboratory.

BACKGROUND OF THE INVENTION

1. Field of the Invention

The present invention relates to acoustic methods and apparatus for monitoring sliver linear density and yarn strength, and more particularly to acoustic methods and apparatus for monitoring sliver linear density and yarn strength based on wave propagation and acoustic resonance.

2. Description of the Prior Art

A need exists for an automated system and an on-line, non-destructive method and apparatus to provide selected data including density and yarn strength that is important in the processing of yarn prior to its use in fabrics or other textile products. Density and yarn strength provide important information to facilitate guidelines on uniformity and strength and other characteristics of the yarn prior to being incorporated into fabric.

It is an object of the present invention to provide an improved method and apparatus for monitoring sliver linear density and yarn strength.

It is another object of the present invention to provide an improved method and apparatus for monitoring sliver linear density and yarn strength using an acoustic probe and a pair of piezoelectric sensors to provide efficient and reliable operation.

It is another object of the present invention to provide an improved method and apparatus for monitoring sliver linear density and yarn strength utilizing a measurement of yarn/slivers' transverse wave velocity which in principle is a function of the stiffness and density of the yarn/sliver.

It is another object of the present invention to provide an improved method and apparatus for monitoring sliver linear density and yarn strength utilizing an acoustic resonance measurement.

It is another object of the present invention to provide an improved method and apparatus for monitoring sliver linear density and yarn strength overcoming some of the disadvantages of known arrangements.

SUMMARY OF THE INVENTION

In brief, these and other objects and advantages of the invention are provided by acoustic methods and apparatus for monitoring sliver or yarn to identify predefined characteristics including linear density and strength based on wave propagation and acoustic resonance. Transverse waves are generated relative to the sliver or yarn. At least one dry-coupled acoustic sensor is in contact with the sliver or yarn for detecting waves coupled to the sliver or yarn and for generating a signal. The generated signal is processed to identify the predefined characteristics including sliver or yarn linear density. The transverse waves can be generated with a focused acoustic transmitter spaced relative to the sliver or yarn with pulses having a central frequency in a range between 20 KHz and 40 KHz applied to the transmitter. The transverse waves can be generated by mechanically agitating the sliver or yarn with a tapping member.

BRIEF DESCRIPTION OF THE DRAWING

These and other objects and advantages of the present invention will become readily apparent upon consideration of the following detailed description and attached drawing, wherein.

DETAILED DESCRIPTION OF THE PREFERRED EMBODIMENT

The invention provides two acoustic techniques that are applied to the on-line monitoring of sliver linear density and yarn strength. The techniques are acoustic resonance and wave propagation methods. The acoustic wave propagation technique is based on the measurement of yarn/sliver's transverse wave velocity which in principle is a function of the stiffness and density of the yarn/sliver. Because of high attenuation of acoustic wave in yarn/sliver, the measurement system needs a relatively high-power, focused acoustic transmitter and sensitive receivers.

Figure 1:
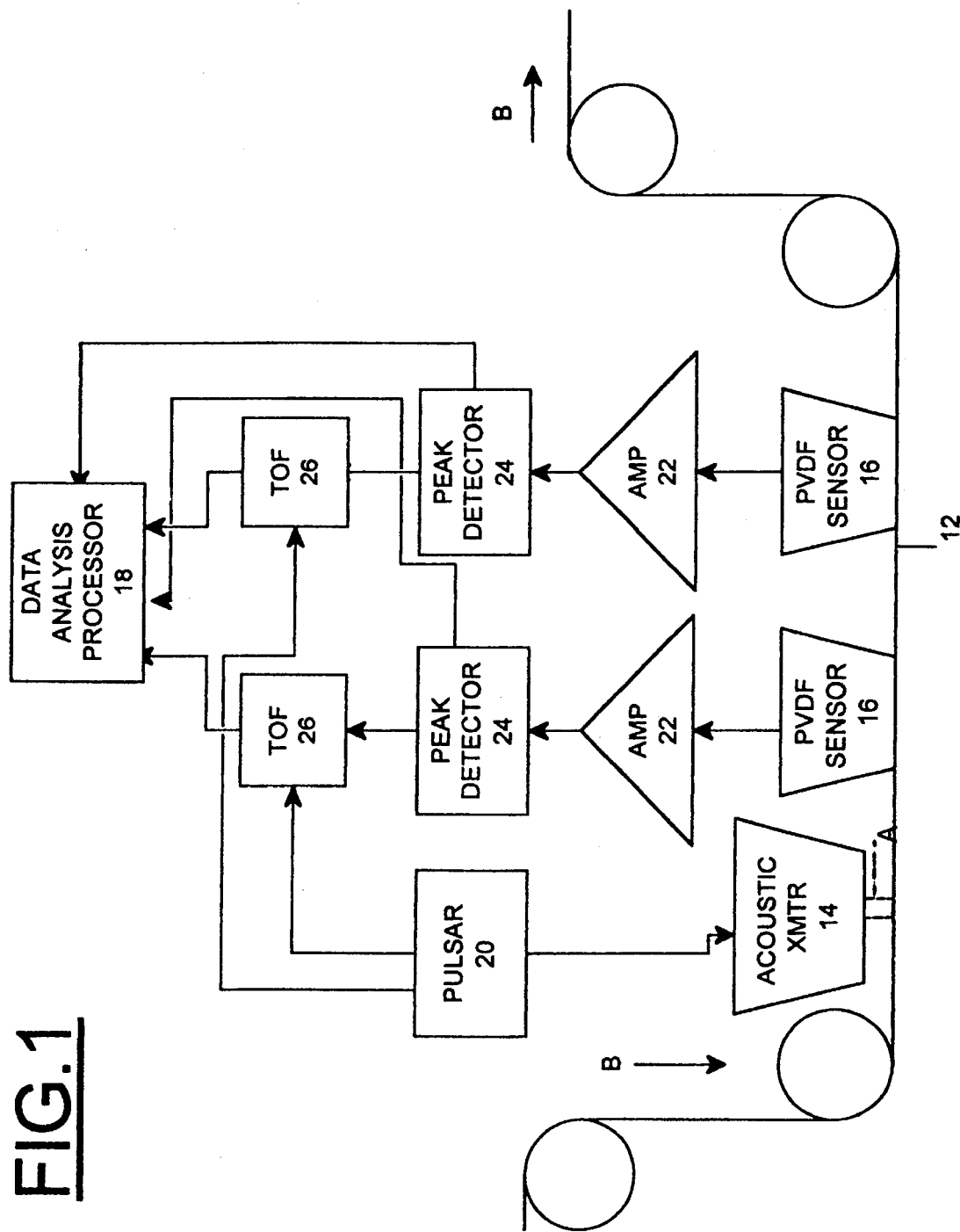
FIG. 1 is a schematic and block diagram representation of a sliver and yarn monitoring system of the invention.

Referring to FIG. 1 of the drawing, there is shown a schematic and block diagram representation of a sliver and yarn monitoring system according to the invention generally designated by the reference numeral 10. Sliver and yarn monitoring system 10 provides on-line monitoring of a sliver or yarn 12 to identify its linear density and strength characteristics. Sliver and yarn monitoring system 10 provides non-destructive monitoring with fast response. Sliver and yarn monitoring system 10 is a simple, low cost arrangement.

Sliver and yarn monitoring system 10 includes an air-coupled acoustic probe or transmitter 14 and a pair of piezoelectric acoustic sensors 16. Sliver and yarn monitoring system 10 includes at least two acoustic sensors 16 spaced apart along the length of the sliver or yarn 12 to be inspected so that the time-of-flight (TOF) and relative amplitude loss can be measured. High-powered, focused acoustic waves indicated by the dashed lines labelled A are transmitted by the transmitter 14 to the sliver or yarn 12 and the generated transverse waves in the sliver or yarn are measured and used to identify linear density and strength characteristics.

Acoustic transmitter 14 transmits high-powered, focused longitudinal sound waves of frequency between 20 KHz through 40 KHz through the air. The acoustic transmitter 14 is a non-contact, air-coupled transducer. Acoustic sensors 16 are non-destructive, dry-contact sensors. Sliver and yarn monitoring system 10 can be operated in an in-line mode with the yarn 12 moving along the transmitter 14 and sensors 16 as indicated by arrows labelled B. The acoustic probe or transmitter 14 produces large-amplitude pulses of central frequency in range between 20 KHz and 40 KHz. Polyvinyl piezoelectric films can be used for the sensors 16. Preferably the sensors 16 are thin-film type, such as polyvinylidene fluoride (PVDF).

Appropriate energies are applied by the probe 14 to generate transverse signals in the sliver or yarn 12 detected by the sensors 16 and then analyzed by a data analysis processor 18. Data analysis processor 18 is suitably programmed to perform the signal analysis in accordance with the invention. During these tests, the yarn 12 is held under tension. A pulser 20 generates a pulse signal applied to the acoustic transmitter 14. A respective detected signal from each acoustic sensor 16 is applied to a respective preamplifier 22 and amplified. Then peak amplitudes and times of flight are measured at a first block 24 labelled PEAK DETECTOR and a second block 26 labelled TOF, respectively. Correlated values of linear density and yarn strength are determined from the time-of-flight (TOF) measurements and relative amplitude loss. The TOF measurement is used to calculate the wave velocity and the amplitude loss predicts the attenuation. Both measurements, TOF and attenuation are related to the linear density and yarn strength.

Figure 2A:
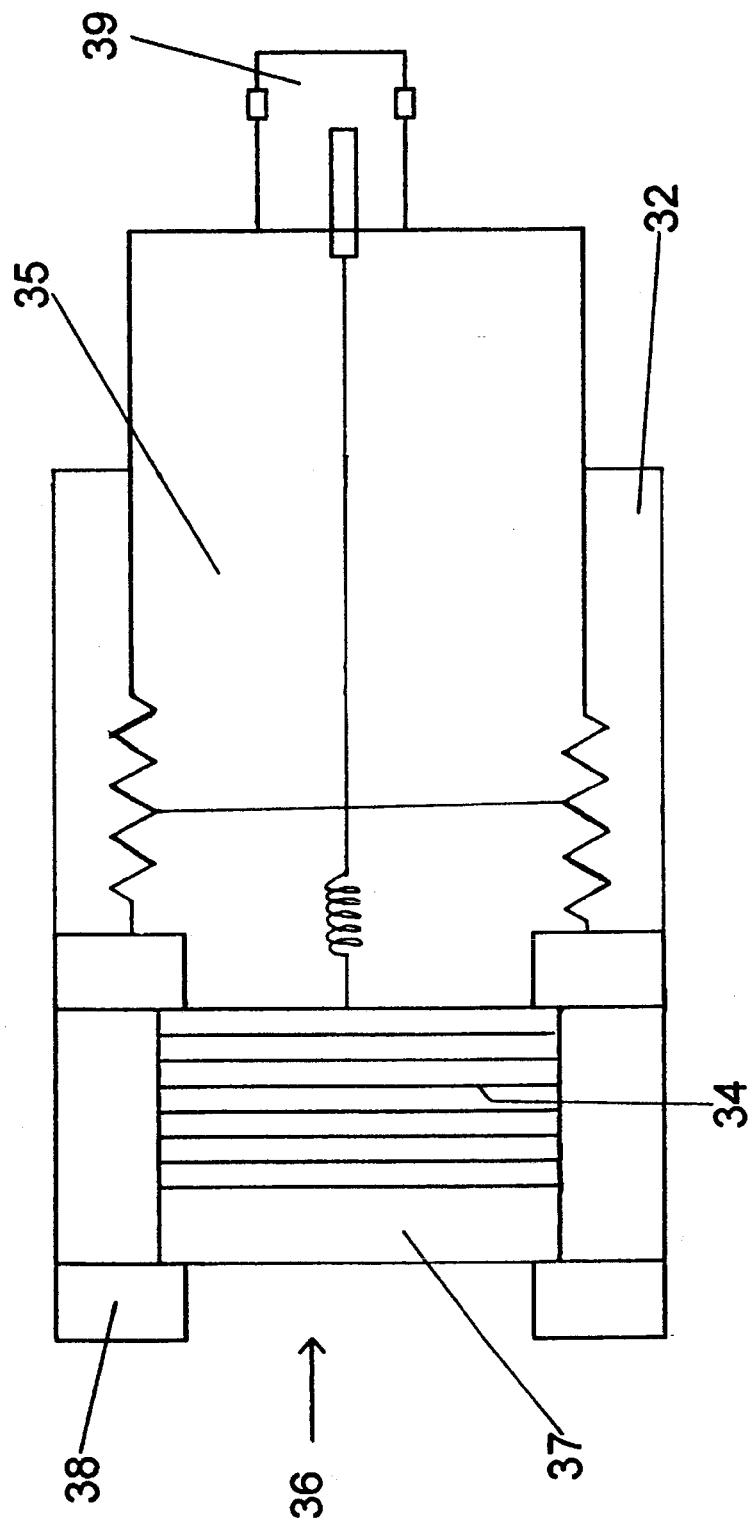
FIG. 2A is a partly schematic side view representation of an acoustic dry-coupled sensor apparatus of the sliver and yarn monitoring system of FIG. 1.

Referring now to FIG. 2A, there is shown a dry-coupled acoustic sensor generally designated by the reference character 30. The dry-coupled sensor 30 includes a threaded housing 32, for example that is formed of steel, for containing a stack of PVDF films 34 at a front end section generally designated 36. The front end section 36 contains a protective coating 37, for example that is formed of epoxy. The PVDF films 34 and the protective coating 37 are positioned in the housing 32 by phenolic spacers 38. A signal that is applied to the acoustic transmitter 14 is applied to the PVDF sensors 34 and output signal leads (not shown) are connected to a connector 39 mounted on a threaded rod 35.

Figure 2B:
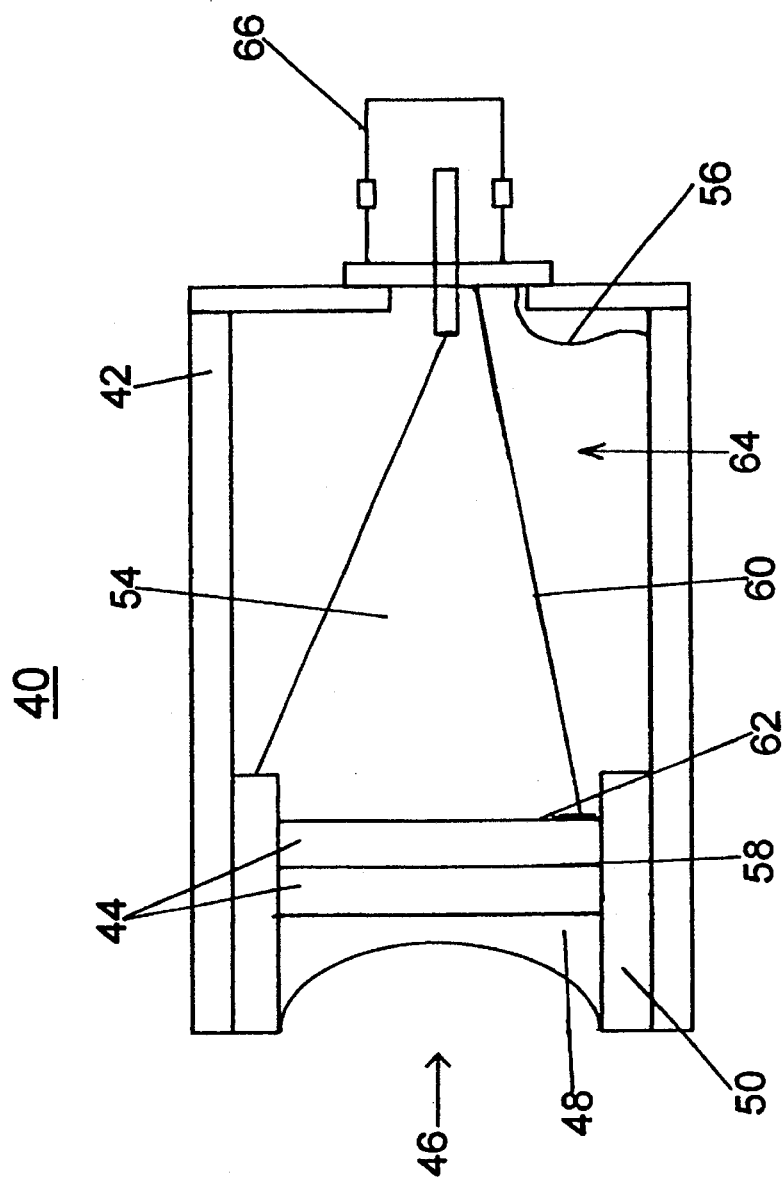
FIG. 2B is a partly schematic side view representation of an air-coupled acoustic probe or transmitter apparatus of the sliver and yarn monitoring system of FIG. 1.

Referring now to FIG. 2B, there is shown an air-coupled transducer generally designated by the reference character 40 that advantageously can be used for the acoustic transmitter 14. Air-coupled transducer 40 includes a housing 42, for example that is formed of steel, for containing a set of crystals 44 at a front-end section generally designated 46. Transducer 40 uses a specifically designated front-end section 46 having a focused curvature design and a special matching material 48 on the outer face of the crystal to improve impedance matching. The preferred matching material 48 is an air-filled epoxy to provide improved matching with the air. Piezoelectric crystals 44 has a high acoustic impedance. Providing air bubbles within the epoxy matching material 48 lowers the acoustic impedance.

Use of a specially designed front-end matching material 48 containing air bubbles allows the transducer 40 to effectively transmit and receive longitudinal waves of frequency between 20 KHz and 40 KHz through the air. Focused piezoelectric crystals can be used for crystals 44. A plurality of phenolic spacers 50 and an epoxy boundary 52 mount crystal 44 within the front-end section 46 of the housing 42. Crystals 44 are supported by a cone-shaped backing mass 54, for example that is formed of brass. A negative lead 56 is connected to a middle surface 58 of the crystals 44. A positive lead 60 is connected to a rear surface 62 of the crystal 44. A lead-filled epoxy cavity filler 64 fills the cavity behind crystals 44 within the housing 42. A connector 66 mounted on the housing 42 is connected to the negative lead 56 and the positive lead 60 for coupling an electrical signal to or from the piezoelectric crystal 44.

Figure 3:
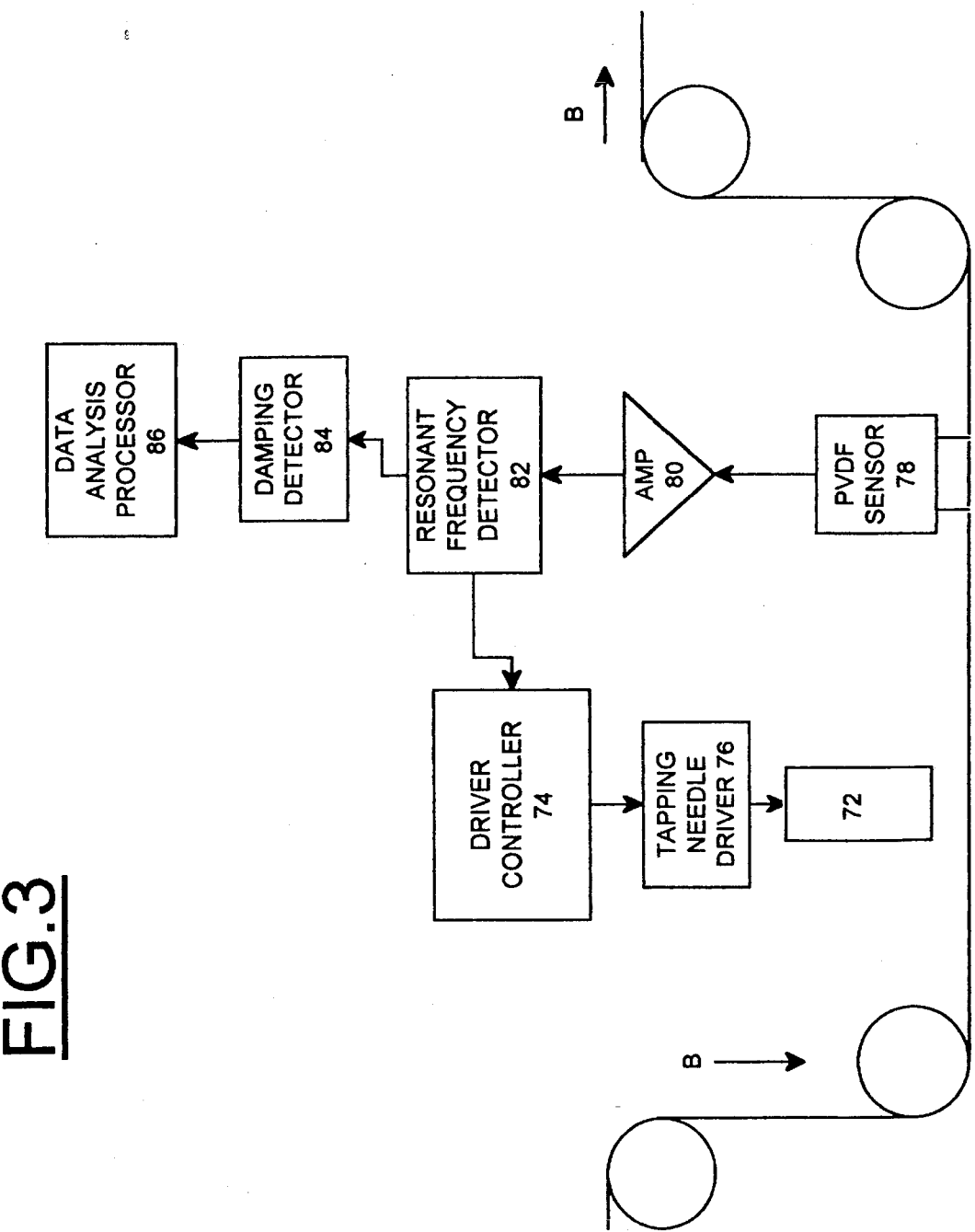
FIG. 3 is a schematic and block diagram representation of an alternative sliver and yarn monitoring system of the invention.

Referring to FIG. 3, there is shown an alternative sliver and yarn monitoring system of the invention generally designated by the reference character 70. In monitoring system 70, yarns and slivers 12 are mechanically agitated with a tapping head or needle 72 with the resonance frequencies and their damping characteristics are measured and correlated with density and yarn strength. Tapping needle 72 is operatively controlled by a driver controller 74 via a tapping needle driver 76. A piezoelectric sensor 78 detects the wave propagation through sliver or yarn 12 that results from the mechanical agitation by the tapping needle 72. Piezoelectric sensor 78 advantageously is an identical type sensor as the acoustic sensor 16 of monitoring system 10. The detected wave propagation from piezoelectric sensor 78 is amplified by an amplifier 80. The amplified signal is applied to a resonant frequency detector 82. The output of the resonant frequency detector 82 is applied to a damping detector block 84 and also provides a feedback signal to the driver controller 74. The output signal of the damping detector block 84 providing measured damping characteristics of the yarn 12 is applied to a data analysis processor 86 and correlated with density and yarn strength.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. Apparatus for monitoring a sliver or yarn to identify predefined characteristics comprising:

means for generating transverse waves into the sliver or yarn;

sensor means responsive to said transverse waves generating means for detecting transverse wave propagation in the sliver or yarn and for generating a responsive signal; said sensor means including at least two thin film, polyvinylidene fluoride (PVDF) piezoelectric sensors; and signal processing means responsive to said sensor means for processing said generated responsive signal to identify the predefined characteristics including sliver or yarn linear density, said signal processing means including a respective peak detector coupled to each of said at least two thin film, polyvinylidene fluoride (PVDF) piezoelectric sensors, each said peak detector for detecting peak values in said generated responsive signal, a respective time-of-flight detector coupled each said peak detector for identifying time-of-flight values and a data analysis processor for identifying relative amplitude loss values, and for utilizing both said identified time-of-flight values and said relative amplitude loss values to determine sliver or yarn linear density.

2. Apparatus for monitoring a sliver or yarn as recited in claim 1 wherein said transverse waves generating means and said sensor means are in contact with the sliver or yarn.

3. Apparatus for monitoring a sliver or yarn as recited in claim 1 wherein said transverse waves generating means include a pair of piezoelectric crystals for generating acoustic waves and an acoustic impedance matching material is disposed on an outer face of the crystals to improve acoustic impedance matching.

4. Apparatus for monitoring a sliver or yarn as recited in claim 3 wherein said acoustic impedance matching material is an air-filled epoxy.

5. Apparatus for monitoring a sliver or yarn as recited in claim 1 wherein said transverse waves generating means include a tapping member.

6. Apparatus for monitoring a sliver or yarn as recited in claim 5 wherein said tapping member is operatively controlled for mechanically agitating the sliver or yarn.

7. Apparatus for monitoring a sliver or yarn as recited in claim 6 wherein said tapping member is operatively controlled by a driver and a driver controller.

8. Apparatus for monitoring a sliver or yarn as recited in claim 1 wherein said generated transverse waves have a frequency in a range between 20 KHz and 40 KHz.

9. Apparatus for monitoring a sliver or yarn as recited in claim 6 wherein said signal processing means responsive to said sensor means for processing said generated responsive signal include a resonant frequency detector for identifying resonance frequency and a damping detector for identifying damping characteristics of the sliver or yarn.

10. Apparatus for monitoring a sliver or yarn as recited in claim 9 wherein said signal processing means responsive to said sensor means for processing said generated responsive signal include a driver controller coupled to said tapping member and wherein said resonant frequency detector applies a feedback signal to said driver controller.

11. A method for monitoring a sliver or yarn to identify predefined characteristics using at least one air-coupled acoustic sensor spaced apart from the sliver or yarn comprising the steps of:

generating transverse waves into the sliver or yarn;

utilizing at least ine thin film, polyvinylidene fluoride (PVDF) piezoelectric sensor spaced apart from a transmitter utilized for generating said transverse waves into the sliver or yarn and detecting traverse wave propagation in the sliver or yarn, measuring time-of-flight and relative amplitude loss with said sensor, and generating a responsive signal; and processing said generated responsive signal to identify the predefined characteristics including sliver or yarn linear density.

12. A method for monitoring a sliver or yarn as recited in claim 11 wherein said step of generating transverse waves relative to the sliver or yarn include the step of providing a high-powered acoustic transmitter spaced relative to the sliver or yarn and providing a pulser for applying large amplitude pulses having a central frequency in a range between 20 KHz and 40 KHz to said transmitter.

13. A method for monitoring a sliver or yarn as recited in claim 11 wherein said step of generating transverse waves relative to the sliver or yarn includes the step of mechanically agitating the sliver or yarn.

14. A method for monitoring a sliver or yarn as recited in claim 13 wherein said step of detecting transverse wave propagation in the sliver or yarn includes the step of utilizing a resonant frequency detector for identifying a resonance frequency of detected wave propagation in the sliver or yarn.

15. A method for monitoring a sliver or yarn as recited in claim 14 further includes the step of measuring damping characteristics of the sliver or yarn, determining the linear density and the yarn strength utilizing the identified resonance frequency and the measured damping characteristics.

* * * * *